United States Patent
Yu et al.

(10) Patent No.: US 11,247,994 B2
(45) Date of Patent: Feb. 15, 2022

(54) 6-DITHIO-SUBSTITUTED-2'-DEOXYGUANOSINE COMPOUND, PREPARATION METHOD THEREOF AND USE THEREOF

(71) Applicant: ZHEJIANG UNIVERSITY, Hangzhou (CN)

(72) Inventors: Lushan Yu, Hangzhou (CN); Su Zeng, Hangzhou (CN); Yang Zhang, Hangzhou (CN)

(73) Assignee: Zhejiang University, Zhejiang (CN)

( * ) Notice: Subject to any disclaimer, the term of this patent is extended or adjusted under 35 U.S.C. 154(b) by 0 days.

(21) Appl. No.: 17/149,747

(22) Filed: Jan. 15, 2021

(65) Prior Publication Data
US 2021/0130356 A1   May 6, 2021

Related U.S. Application Data

(63) Continuation of application No. PCT/CN2019/092094, filed on Jun. 20, 2019.

(30) Foreign Application Priority Data

Aug. 30, 2018   (CN) .......................... 201811003442.6

(51) Int. Cl.
*C07D 473/24* (2006.01)
(52) U.S. Cl.
CPC .................. *C07D 473/24* (2013.01)
(58) Field of Classification Search
None
See application file for complete search history.

(56) References Cited

FOREIGN PATENT DOCUMENTS

| CN | 109053841 A | 12/2018 |
| WO | 0233128 A2 | 4/2002 |
| WO | 2004094447 A1 | 11/2004 |

OTHER PUBLICATIONS

"Synthetic nucleosides and nucleotides. X. Synthesis and biological activities of several purin-6-yl benzyl disulfides and their ribonucleosides" Saneyoshi, Mineo et al. [Dec. 31, 1978] p. 169, figure 1, compound 8, and pp. 169-172, table I-V.
"Selective Inhibition of Extracellular Thioredoxin by Asymmetric Disulfides" Thomas R. DiRaimondo et al. [Jan. 17, 2013] pp. 1301-1310.
"Preparation of Oligodeoxynucleotides Containing 6-Methylthiopurine Residues by Chemical Synthesis or Specific Methylation" Yao-Zhong Xu et al. [Feb. 16, 2007] pp. 929-933.
"S-allyl derivatives of 6-mercaptopurine are highly potent drugs against human B-CLL through synergism between 6-mercaptopurine and allicin" Talia Miron et al. [Sep. 4, 2012] pp. 1536-1540.
"Synthesis and biological evaluation of disulfides bearing 1,2,4-triazole moiety as antiproliferative agents" Xue-Feng Wang et al. [Sep. 5, 2017] pp. 3367-3374.
International Search Report (PCT/CN2019/092094); dated Sep. 26, 2019.

*Primary Examiner* — Craig D Ricci
(74) *Attorney, Agent, or Firm* — W&G Law Group (57) ABSTRACT

The present invention provides a 6-dithio-substituted-2'-deoxyguanosine compound and a preparation method thereof and use thereof in anti-tumor drugs. According to the present invention, a series of brand-new thioredoxin-1 (Trx-1) inhibitors are designed and synthesized by using 2'-deoxyguanosine as a structure mother nucleus. The compound according to the present invention is a structure of formula I, and Trx-1 activity inhibition testing is performed on the type of compounds, showing apparent inhibitory activity. It is indicated from in vitro and in vivo researches that these compounds show significant anti-tumor effects on multiple types of tumors, can be applied to drugs for tumors related to human body cell proliferation, and provide a new path for the research of anticancer drugs.

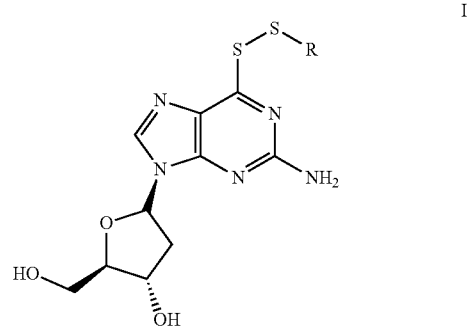

2 Claims, 3 Drawing Sheets

6-DITHIO-SUBSTITUTED-2'-DEOXYGUANOSINE COMPOUND, PREPARATION METHOD THEREOF AND USE THEREOF

CROSS-REFERENCE TO RELATED APPLICATIONS

The present application is continuation of International Patent Application No. PCT/CN2019/092094, filed on Jun. 20, 2019, which claims priority to Chinese patent application NO. 201811003442.6, filed on Aug. 30, 2018, the entire contents of which are incorporated herein by their references.

TECHNICAL FIELD

The present invention relates to the technical field of medicinal chemistry, and in particular, to a 6-dithio-substituted-2'-deoxyguanosine compound, a preparation method thereof and a use thereof in anti-tumor drugs.

BACKGROUND

Cancer is the most important disease that harms human health. According to the latest cancer statistics in China in January 2019, in 2015 (the statistics is 3 years later), there were about 3.929 million malignant tumors and 2.338 million deaths in China, and malignant tumor deaths accounted for 23.9% of all deaths of residents. In 2018, there were 18.1 million new cancer cases and 9.6 million cancer deaths worldwide. Because of the high heterogeneity of tumors, some anti-tumor drugs can only be effective for certain tumors or certain types of tumors, and they are very resistant with repeated administration, which makes the recurrence rate and mortality rate of tumors remain high. Therefore, the research and development of anti-cancer drugs has always been a hot spot in the research and development of new drugs.

At present, 5-FU combined with oxaliplatin or irinotecan is commonly used in the treatment of colorectal cancer, but the effect is not good, especially for patients in the advanced stage. Although the incidence of malignant melanoma is low in clinic, there is no good treatment for metastatic malignant melanoma in clinic at present. The first-line drug dacarbazine has limited curative effect and great toxic and side effects. Therefore, it is necessary to develop drugs for colorectal cancer and melanoma with good curative effect and low toxic and side effects, and it also has a very good market prospect.

Thioredoxin-1 (Trx-1) is cellular redox protein of a low molecular weight that promotes tumor growth, inhibits apoptosis, and upregulates the hypoxia-inducible factor-la and vascular endothelial growth factor. Trx-1 has always been a hot target for discovering new anticancer drugs. Studies have shown that the disulfide compound PX-12 is a new thioredoxin inhibitor, and its chemical name is 1-methylpropyl-2-imidazolyl disulfide. Its disulfide bond is the key active region of the drug molecule, which triggers its molecular targeted anticancer effect by reducing the activities of thioredoxin reductase and thioredoxin. At present, the mechanisms of promoting tumor growth by Trx-1 and inhibiting tumor by PX-12 have been fully studied at home and abroad, and the structure-activity relationship and structural optimization of PX-12 have also been studied. Although PX-12 did not show significant antitumor effect on patients with advanced pancreatic cancer (patients who failed first-line chemotherapy) in Phase II clinical trials, its therapeutic effect on colorectal cancer is still worth being expected.

Telomere is located at the end of aneukaryotic linear chromosome, which plays a role in maintaining integrity of the chromosome and controlling the cell division cycle. Due to "terminal replication problem", oxidative damage and other terminal processing events related to replication, telomere is gradually shortened in each round of DNA replication in normal somatic cells. The telomerase reduces telomere shortening by adding a hexamer telomere DNA (TTAGGG) to the end of a linear chromosome in cell. Therefore, in telomerase negative cells, cells will undergo replication aging because of telomere shortening, but in telomerase positive cells, cells will be immortalized and may develop into cancer. Most normal somatic cells have no telomerase activity, except germ cells, stem cells and activated lymphocytes, but it is almost universally detected in about 85% to 90% of primary human cancers. In recent years, more and more attention has been paid to drug design and research on telomerase targets. Compared with other methods, it has higher tumor specificity and less side effects, mainly including four categories: ① direct inhibition of telomerase activity; ② targeting telomere integrity directly to promote rapid telomere dysfunction and cancer growth inhibition; ③ vaccine targeting telomerase; ④ among the viruses targeting telomerases, the direct inhibition of telomerase activity is the most studied one. At present, there are many candidate drugs for this target in clinical trials, such as imetelstat, GV1001, GRNVAC1 and so on. 2-deoxyguanosine compound 6-thio-dG is a newly discovered small molecule telomerase inhibitor. Its chemical name is nucleoside 6-thio-2'-deoxyguanosine, which can be recognized by telomerases and integrated into de novo synthesized telomeres, resulting in telomere dysfunction. Except germ cells, stem cells and activated lymphocytes, most normal human cells do not have telomerase activity, but it is almost universally detected in about 85% to 90% of primary human cancers. Therefore, these drugs have a broad-spectrum tumor inhibitory effect. At present, 6-thio-dG is in the preclinical development stage, and it is expected that a phase I clinical study will be conducted in the second and third quarters of 2019.

To sum up, Trx-1 and telomerase play a key role in the occurrence and development of tumors. Our research group has designed a variety of dual-target small molecular compounds with both Trx-1 and telomerase inhibitory effects, and obtained promising candidate drugs A, B, C, D for the treatment of colon cancer and melanoma. Through the implementation of this project, the comprehensive evaluation of the pharmaceutical properties of candidate drugs A, B, C and D is completed, and the preclinical evaluation of A, B, C and D is basically completed according to the application requirements, so as to promote the innovative candidate drugs with independent intellectual property rights to stand out and lay a foundation for the subsequent clinical research of new drugs.

The implementation of this project will strengthen and enhance China's research and development capabilities in anti-tumor innovative drugs, promote the research and development of anti-tumor innovative drugs with China's independent intellectual property rights, and provide scientific and technological support and guarantee for China's pharmaceutical industry. At the same time, it has important strategic significance for the population health, social and economic sustainable development of our country.

SUMMARY

The present invention provides a 6-dithio-substituted-2'-deoxyguanosine compound and a preparation method and application thereof, and the enzyme activity test and antitumor activity (cell growth inhibition activity test and nude mouse tumor bearing test) of the compound have achieved relatively good effects.

A 6-dithio-substituted-2'-deoxyguanosine compound having a structure of formula I:

Formula I wherein R is C1-8 alkyl, C1-8 fluoroalkyl, C1-8 chloroalkyl, C1-8 hydroxyalkyl, C1-8 ketoalkyl, —(C1-4 alkyl) R1, —(C1-4 alkyl) NH$_2$, —(C1-4 alkyl) NH (C1-4 alkyl), phenyl selectively substituted by R2, a 5-membered aromatic ring selectively substituted with R2, C3-6 cycloalkyl selectively substituted with R2, or a 5 to 6-membered heteroaromatic ring containing at least one nitrogen and selectively substituted with R2;

R1 is phenyl, phenyl selectively substituted with —F, —Cl, —OH, —NH$_2$, —C1-4 alkyl, —OCH$_3$, —CONH$_2$ or —CONHCH$_3$, or a 5 to 6-membered heteroaromatic ring containing at least one nitrogen atom and selectively substituted with R2; and

R2 is C1-4 alkyl, —CN, —OH, —OMe, —NH$_2$, —NHMe, —N(CH$_3$)$_2$, —F, —CF$_3$, —CO(C1-4 alkyl), —COCH$_2$CH$_2$OH, or —CONHCH$_3$.

Further preferably, the 6-dithio-substituted-2'-deoxyguanosine compound is 6-(sec-butyl dithio)-2'-deoxyguanosine having a structure of formula A, 6-(p-fluorobenzyl dithio)-2'-deoxyguanosine having a structure of formula B, 6-(tert-butyl dithio)-2'-deoxyguanosine having a structure of formula C, or 6-(isopropyl dithio)-2'-deoxyguanosine having a structure of formula D;

A: 6-(sec-butyl dithio)-2'-deoxyguanosine

B: 6-(p-fluorobenzyl dithio)-2'-deoxyguanosine

C: 6-(tert-butyl dithio)-2'-deoxyguanosine

D: 6-(isopropyl dithio)-2'-deoxyguanosine

Another object of the present invention is to provide a preparation method of the 6-dithio-substituted-2'-deoxyguanosine compound as mentioned above, which can be effected by steps of a synthesis reaction formula as follows:

wherein R is as defined in general formula I.

A preparation method of the 6-dithio-substituted-2'-deoxyguanosine compound as mentioned above, comprising the following steps of:

1) adding a compound 1, acetonitrile, acetic anhydride and triethylamine into a reactor, then adding 4-dimethylaminopyridine, stirring and reacting for 10-26 h (more preferably 16-20 h, most preferably 18 h) under protection of nitrogen to precipitate a white solid, and performing filtering and washing to obtain a compound 2;

2) adding the compound 2 and dichloromethane into a reactor, then sequentially adding triethylamine, 2,4,6-trimethylbenzenesulfonyl chloride and 4-dimethylaminopyridine, heating to reflux under the protection of nitrogen after the addition, stirring and reacting for 10-24 h (more preferably 14-18 h, most preferably 16 h), then quenching the reaction with water, cooling the extracted reaction solution to 0-5° C. in an ice water bath, adding a dichloromethane solution of N-methylpyrrolidine dropwise, and continuing stirring in the ice water bath for 0.3-1.5 h (more preferably 0.5 h) after the dropwise addition, stirring at an ambient temperature of 15-35° C. for 0.3-1.5 h, cooling the reaction solution to 0-5° C. with the ice water bath again, adding a dichloromethane solution of thioacetic acid dropwise, keeping the temperature in the reactor at 0-6° C. (more preferably 5° C.), naturally raising the temperature to the ambient temperature of 15-35° C. after the dropwise addition, stirring and reacting for 10-24 h (more preferably 14-18 h, most preferably 16 h), quenching the reaction with water after the reaction is completed, and then performing extraction with dichloromethane, and performing washing and drying to obtain a compound 3;

3

3) dissolving mercaptan having a structure of formula 5 and thiourea in H₂O and ethanol in a reactor, cooling to 0-5° C. in an ice water bath, adding concentrated hydrochloric acid dropwise and then adding H₂O₂ dropwise while keeping the temperature in the reactor at 0-6° C. (more preferably 5° C.), naturally heating to 15-35° C. under protection of nitrogen after the dropwise addition to react for 10-24 h (more preferably 14-18 h, most preferably 16 h), and then performing filtering and washing to obtain semicarbazide (dithioxy) imide having a structure of formula 6;

5

6

14) adding the compound 3, semicarbazide (dithioxy) imide having the structure of formula 6 and methanol into a reactor, then adding an aqueous solution of NaHCO₃ dropwise, reacting for 10-24 h (more preferably 14-18 h, most preferably 16 h) at the ambient temperature of 15-35° C. after the dropwise addition, and obtaining a compound 4 after post-treatment;

4

5) adding the compound 4 and methanol into a reactor, adding ammonia water into the reactor dropwise, reacting for 10-24 h (more preferably 14-18 h, most preferably 16 h) at the ambient temperature of 15-35° C. after the dropwise addition, and obtaining the 6-dithio-substituted-2'-deoxyguanosine compound having the structure of formula I after post-treatment;

I wherein R in each of formula 5, formula 6 and formula 4 has the same meaning as R in formula I.

In the step 1), a dosage ratio of the compound 1, acetonitrile, acetic anhydride, triethylamine and 4-dimethylaminopyridine is 50-70 mmol:130-170 mL:150-210 mmol:250-350 mmol:3-9 mmol. More preferably, the dosage ratio of the compound 1, acetonitrile, acetic anhydride, triethylamine and 4-dimethylaminopyridine is 55-65 mmol:140-160 mL:17-190 mL:280-320 mmol:5-7 mmol. Most preferably, the dosage ratio of the compound 1, acetonitrile, acetic anhydride, triethylamine and 4-dimethylaminopyridine is 60 mmol:150 mL:180 mmol:300 mmol:6 mmol.

In the step 2), a dosage ratio of the compound 2, dichloromethane, triethylamine, 2,4,6-trimethylbenzenesulfonyl chloride, 4-dimethylaminopyridine, the dichloromethane solution of N-methylpyrrolidine and the dichloromethane solution of thioacetic acid is 15-25 mmol:150-250 mL:5-15 mL:30-50 mmol:2-6 mmol:10-30 mL:20-40 mL. More preferably, the dosage ratio of the compound 2, dichloromethane, triethylamine, 2,4,6-trimethylbenzenesulfonyl chloride, 4-dimethylaminopyridine, the dichloromethane solution of N-methylpyrrolidine and the dichloromethane solution of thioacetic acid is 18-22 mmol:180-220 mL:8-12 mL:35-45 mmol:3-5 mmol:15-25 mL:25-35 mL. Most preferably, the ratio of the compound 2, dichloromethane, triethylamine, 2,4,6-trimethylbenzenesulfonyl chloride, 4-dimethylaminopyridine, the dichloromethane solution of N-methylpyrrolidine and the dichloromethane solution of thioacetic acid is 20 mmol:200 mL:10 mL:40 mmol:4 mmol:20 mL:30 mL.

The dichloromethane solution of N-methylpyrrolidine consists of N-methylpyrrolidine and dichloromethane in a volume ratio of 1:0.5-1.5, and the dichloromethane solution of thioacetic acid consists of thioacetic acid and dichloromethane in a volume ratio of 1:1-3. Most preferably, the dichloromethane solution of N-methylpyrrolidine consists of N-methylpyrrolidine and dichloromethane in a volume ratio of 1:1 and the dichloromethane solution of thioacetic acid consists of thioacetic acid and dichloromethane in a volume ratio of 1:2.

In the step 3), a dosage ratio of the mercaptan having the structure of formula 5, thiourea, $H_2O$, ethanol, concentrated hydrochloric acid and $H_2O_2$ is 50-80 mmol:40-60 mmol:15-30 mL:50-80 mL:4-7 mL:5-8 mL. More preferably, the dosage ratio of the mercaptan having the structure of formula 5, thiourea, $H_2O$, ethanol, the concentrated hydrochloric acid and $H_2O_2$ is 60-70 mmol:45-55 mmol:20-25 mL:60-70 mL:5-6 mL:6-7 mL. Most preferably, the dosage ratio of the mercaptan having the structure of formula 5, thiourea, $H_2O$, ethanol, concentrated hydrochloric acid and $H_2O_2$ is 65 mmol:50 mmol:22.5 mL:65 mL:5.5 mL:6.5 mL.

A mass percentage of the concentrated hydrochloric acid is 35%-37%.

In the step 4), a dosage ratio of the compound 3, semicarbazide (dithioxy) imide, methanol and the aqueous solution of $NaHCO_3$ is 1-2.5 g:2-8 mmol:15-35 mL:5-10 mL, and the aqueous solution of $NaHCO_3$ consists of $NaHCO_3$ and water in a dosage ratio of 5-10 mmol:5-10 mL. More preferably, the dosage ratio of the compound 3, semicarbazide (dithioxy) imide, methanol and the aqueous solution of $NaHCO_3$ is 1.3-1.7 g:4-6 mmol:22.5-27.5 mL:6-9 mL, and the aqueous solution of $NaHCO_3$ consists of $NaHCO_3$ and water in a ratio of 6-9 mmol:6-9 mL. Most preferably, the dosage ratio of the compound 3, semicarbazide (dithioxy) imide, methanol and the aqueous solution of $NaHCO_3$ is 1.5 g:5 mmol:25 mL:7.5 mL, and the aqueous solution of $NaHCO_3$ consists of $NaHCO_3$ and water in a dosage ratio of 7.5 mmol:7.5 mL.

In the step 5), a dosage ratio of the compound 4, methanol and ammonia water is 1-3 mmol:20-60 mL:20-60 mL. More preferably, the dosage ratio of the compound 4, methanol and ammonia water is 1.5-1.5 mmol:35-45 mL:35-45 mL. Most preferably, the dosage ratio of the compound 4, methanol and ammonia water is 2 mmol:40 mL:40 mL.

Another object of the present invention is to provide a use of the 6-dithio-substituted-2'-deoxyguanosine derivatives in manufacture of antitumor drugs. Pharmacological studies prove that the compounds provided by the present invention can be used for inhibiting the activities of thioredoxin reductase and thioredoxin (TrxR/Trx-1), and can also be used for treating cancers.

The 6-dithio-substituted-2'-deoxyguanosine derivatives can be used for preparing anti-tumor drugs with inhibitory effect on various cancer cells, and the anti-tumor drugs comprise one or more (including two) drugs for preventing or/and treating colon cancer, lung cancer, skin melanoma, breast cancer, leukemia, liver cancer and gastric cancer.

The antitumor drugs are used for inhibiting the activity of thioredoxin Trx.

Compared with the prior art, the present invention has the following advantages:

The 6-dithio-substituted-2'-deoxyguanosine derivatives of the present invention were discovered by our research group during the system structural modification of PX-12 and 6-thio-dG, which are new compounds not reported in literature and have completely independent intellectual property rights. In vitro and in vivo anti-tumor activity studies show that their growth inhibitory activities on different tumor cells are generally higher than that of their analogues PX-12 and 6-thio-dG, with a high efficiency and a broad spectrum, and a relatively low toxicity; researches on the mechanism of action showed that the compounds not only inhibit the activities of thioredoxin reductase and thioredoxin (TrxR/Trx-1), but also block telomerases, and have a double-target effect.

BRIEF DESCRIPTION OF DRAWINGS

FIG. 4(a) shows changes of the body weight and FIG. 4(b) shows changes of the tumor volume.

DESCRIPTION OF EMBODIMENTS

The present invention will be further explained with examples. The following examples are intended to illustrate the present invention, but not to limit the present invention in any way.

Example 1 (Preparation of Diacetyl-2'-deoxyguanosine 2)

A compound 1 (17.11 g, 60 mmol), MeCN (acetonitrile, 150 mL), Ac₂O (acetic anhydride, 18.38 g, 180 mmol) and TEA (triethylamine, 30.36 g, 300 mmol) were added into a 500 ml single-neck bottle in turn, and then DMAP (4-dimethylaminopyridine, 0.73 g) was added slowly, after the addition, the mixture was stirred overnight (18 h) at room temperature of 25° C. under nitrogen protection; a large number of white solids were precipitated, and the reaction was complete by TLC; the reaction was stopped, suction filtration was carried out, the filter cake was washed with MeCN (10 mL×3), and then drained with an oil pump, obtaining 20.1 g of a compound 2 (confirmed as the compound having a structure of formula 2 by the relevant spectrum data) as a white solid with a yield of 95.2%.

Example 2 (Preparation of Diacetyl-6-thio-2'-deoxyguanosine 3)

The compound 2 (7.03 g, 20 mmol) and DCM (dichloromethane, 200 mL) were added into a 250 mL three-necked bottle, and then TEA (triethylamine, 10 mL), 2,4,6-trimethylbenzenesulfonyl chloride (8.75 g, 40 mmol) and DMAP (4-dimethylaminopyridine, 0.49 g, 0.49 g) were added successively into a 250 ml three mouthed bottle; after addition, the mixture was heated to reflux under the protection of nitrogen and stirred overnight (16 h); sampling was carried out and the sample was quenched with water; after extraction, the reaction solution was cooled to 0-5° C. in an ice water bath; the DCM (10 ml) solution of N-methylpyrrolidine (10 ml) was added dropwise; after the dropwise addition, the mixture was stirred for 0.5 h in ice water bath, and then stirred for 0.5 h at room temperature of 25° C.; after the reaction solution was cooled to 0-5° C. in ice water bath again, the DCM (dichloromethane, 20 ml) solution of thioacetic acid (10 ml) prepared in advance was added dropwise, and the internal temperature was kept at 5° C.; after the dropwise addition, the reaction solution was naturally heated to room temperature of 25° C. and stirred overnight (16 h); after the reaction was completed, water (100 ml) was added to quench, then DCM (dichloromethane, 100 ml×4) was used to perform extraction; the reactant was washed with saturated NaCl water (100 ml) once, and was dried with anhydrous sodium sulfate; silica gel was mixed with the sample and spin dried, and passed through the column (DCM→DCM:methanol MeOH=100:1-50:1-20:1-10:1), obtaining 5 g of a compound 3 (confirmed as the compound having a structure of formula 3 by the related spectrum data) as a light yellow solid with a yield of 71%.

Example 3 (Preparation of Sec-Butyl Semicarbazide(dithioxy) imide)

Sec-butyl mercaptan (5.86 g, 65 mmol) and thiourea (3.81 g, 50 mmol) were dissolved in H₂O (22.5 mL) and EtOH (ethanol, 65 mL), cooled to 0-5° C. in an ice water bath, then concentrated hydrochloric acid (36.5%, 5.5 ml) was slowly added dropwise, and then H₂O₂ was added dropwise; after the dropwise addition, H₂O₂ (6.5 ml) was added dropwise, and the internal temperature was kept at 5° C.; after the dropwise addition, the temperature was naturally raised to 25° C. under the protection of nitrogen, and the mixture was reacted was overnight (16 h); a crude product of sec-butyl semicarbazide (dithioxy) imide was obtained by direct rotary drying and oil pump drying.

Example 4 (Preparation of Diacetyl-6-dithiotert-butyl-2'-deoxyguanosine 4a)

The compound 3 (the crude product, 1.5 g), sec-butyl semicarbazide (dithioxy) imide (1.84 g, 5 mmol) and MeOH (25 mL) were added into a 100 mL single-necked bottle, and then the pre-prepared H₂O (7.5 mL) solution of NaHCO₃ (0.63 g, 7.5 mmol) was added dropwise. After the dropwise addition, the solution reacted overnight (16 h) under stirring at the room temperature of 25° C. After the reaction was completed, silica gel was added, mixed, spin dried, and passed through the column (DCM→DCM:MeOH=100:1→50:1→20:1). 1.2 g of compound 4a (confirmed as a compound having the structure of formula 4a by the relevant spectrum data) was obtained as a light yellow oily solid.

Example 5 (Preparation of 6-(sec-butyl dithio)-2'-deoxyguanosine a)

A compound 4a (0.91 g, 2 mmol) and MeOH (40 mL) were added into a 100 mL single-necked bottle, and then ammonia water (40 mL) was slowly added dropwise; after the dropwise addition, the mixture reacted overnight (16 h) under stirring at room temperature of 25° C.; TLC (thin layer chromatography) showed that the reaction was complete, and the reaction was stopped, the mixture was spin dried and dried by oil pump, obtaining 0.7 g of a compound A as a beige solid with a purity of 96%.

The characterization data of the compound A is as follows:

¹H NMR (DMSO-D₆, 600 MHz) δ8.17 (s, 1H), 6.59 (s, 2H), 6.14 (t, J=6.0 Hz, 1H), 6.25 (d, J=4.2 Hz, 1H), 4.93-4.90 (m, 1H), 4.29 (s, 1H), 3.75-3.41 (m, 1H), 3.51-3.48 (m, 1H), 3.44-3.41 (m, 1H), 3.03-3.01 (m, 1H), 2.56-2.51 (m, 1H), 2.17-2.14 (m, 1H), 1.59-1.54 (m, 1H), 1.45-1.40 (m, 1H), 1.18 (d, J=6.0 Hz, 3H), 0.88 (t, J=6.0 Hz, 3H); ¹C NMR (DMSO-D₆, 151 MHz) δ159.8, 158.2, 151.4, 139.8, 124.4, 87.7, 82.9, 70.8, 61.7, 47.5, 40.1, 28.3, 19.6, 11.3; MS (ESI) (m/z): calcd for $C_{14}H_{21}N_5O_3S_2(M+H^+)$: 372.11; Found: 372.27.

Example 6 (Preparation of 6-(p-fluorobenzyl dithio)-2'-deoxyguanosine B)

The preparation method was the same as that in Examples 3-5, except replacing sec-butyl mercaptan with p-fluorobenzyl mercaptan; thiourea was reacted with p-fluorobenzyl mercaptan in concentrated hydrochloric acid and hydrogen peroxide, the obtained p-fluorobenzyl semicarbazide (dithioxy) imide was then reacted with the compound 3 in the presence of sodium bicarbonate, and finally hydrolyzed with ammonia water to obtain 0.6 g of a compound B as a beige solid with purity of 96%.

The characterization data of the compound B is as follows:

$^1$H NMR (DMSO-D$_6$, 600 MHz) δ8.25 (d, J=3.0 Hz, 1H), 7.40 (t, J=7.2 Hz, 2H), 7.12 (t, J=8.4 Hz, 2H), 6.77 (s, 2H), 6.25-6.23 (m, 1H), 5.34 (t, J=3.6 Hz, 1H), 5.01 (d, J=5.4 Hz, 1H), 4.38 (s, 1H), 4.23 (s, 2H), 3.84 (m, 1H), 3.59-3.57 (m, 1H), 3.52-3.50 (m, 1H), 2.63-2.61 (m, 1H), 2.26-2.23 (m, 1H); $^{13}$C NMR (DMSO-D$_6$, 151 MHz) δ161.6 (d, J=243.6 Hz), 159.9, 157.9, 151.5, 139.8, 132.8, 131.8 (d, J=8.3 Hz), 124.4, 115.2 (d, J=21.3 Hz), 87.8, 82.9, 70.7, 61.7, 41.0, 40.1; MS(ESI)(m/z): calcd for C$_{17}$H$_{18}$FN$_5$O$_3$S$_2$(M+H$^+$): 423.08; Found: 424.39.

Example 7 (Preparation of 6-(tert-butyldithio)-2'-deoxyguanosine C)

The preparation method was the same as that in Examples 3-5, except replacing sec-butyl mercaptan with tert-butyl mercaptan; thiourea was reacted with tert-butyl mercaptan in concentrated hydrochloric acid and hydrogen peroxide, the obtained tert-butyl semicarbazide (dithioxy) imide was then reacted with the compound 3 in the presence of sodium bicarbonate, and finally hydrolyzed with ammonia water to obtain 0.59 g of a compound C as a light yellow powder with a purity of about 95%.

The characterization data of the compound C is as follows:

$^1$H NMR (CDCl$_3$, 600 MHz) δ7.75 (s, 1H), 6.26-6.23 (m, 1H), 5.64 (br, 2H), 5.34 (s, 2H), 4.74 (d, J=5.4 Hz, 1H), 4.20 (s, 1H), 3.96 (d, J=12.6 Hz, 1H), 3.77 (d, J=12.0 Hz, 1H), 2.99-2.95 (m, 1H), 2.30-2.27 (m, 1H), 1.34 (s, 9H); $^{13}$C NMR (CDCl$_3$, 151 MHz) δ162.1, 158.5, 149.6, 140.5, 126.9, 89.4, 87.6, 73.4, 63.6, 49.7, 40.5, 30.0; MS (ESI) (m/z): calcd for C$_{14}$H$_{21}$N$_5$O$_3$S$_2$ (M+H$^+$):371.11; Found: 372.23.

Example 8 (Preparation of 6-(isopropyl dithio)-2'-deoxyguanosine D)

The preparation method was the same as that in Examples 3-5, except replacing sec-butyl mercaptan with isopropyl mercaptan; thiourea was reacted with isopropyl mercaptan in concentrated hydrochloric acid and hydrogen peroxide, the obtained isopropyl semicarbazide (dithioxy) imide was then reacted with the compound 3 in the presence of sodium bicarbonate, and finally hydrolyzed with ammonia water to obtain 0.62 g of a compound D as white powder with purity of about 98%.

The characterization data of the compound D is as follows:

$^1$H NMR (CDCl$_3$, 600 MHz) δ7.76 (s, 1H), 6.34 (d, J=12.0 Hz, 1H), 6.26-6.23 (m, 1H), 5.39 (s, 2H), 4.72 (d, J=4.8 Hz, 1H), 4.19 (s, 1H), 3.93 (d, J=12.6 Hz, 1H), 3.75 (d, J=12.0 Hz, 1H), 3.23-3.19 (m, 1H), 2.96-2.91 (m, 1H), 2.67-2.51 (m, 1H), 2.30-2.27 (m, 1H), 1.31 (s, 3H), 1.30 (s, 3H); $^{13}$C NMR (CDCl$_3$, 151 MHz) δ162.0, 158.6, 149.7, 140.5, 126.8, 89.2, 87.4, 73.1, 63.5, 41.8, 40.4, 22.51, 22.47; MS (ESI) (m/z): calcd for C13H$_{19}$N$_5$O$_3$S$_2$ (M+H$^+$):357.09; Found: 358.04.

Biological Experiment 1:

Ellman Test—Inhibitory Effect of 6-dithio-substituted-2'-deoxyguanosine Derivative Analogues on TrxR/Trx-1 Activity A TrxR/TR experiment based on the Ellman reaction was used to determine the inhibitory activity of candidate compounds. Ellman reaction is that 5,5'-dithiobis (2-nitrobenzoic acid) (DTNB) reacts with sulfhydryl (—SH) to form a yellow substance with absorption at 412 nm. The increase of absorption can be equivalent to the decrease of NADPH mediated by TrxR, thus further judging the activity of TrxR/Trx-1. All experiments were carried out on 96-well plates. Before the start of the enzyme reaction, five groups of corresponding test compound stock solutions with different concentrations were prepared. In the TrxR/Trx-1 reaction, a total volume per well was 60 μL, including 100 mM HEPES, 5 mM EDTA (HE buffer, pH 7.5), 1 mM NADPH, 1.0 μM TrxR, 0.8 μM Trx-1, 2.5 mg/mL bovine insulin and the required concentration of compounds to be tested. No compound to be tested was added to the control group. No compound to be tested, TrxR and Trx-1 were added in the blank group. The plate was shaken on an oscillator for 30 seconds to fully mix the reactants. After incubation at 37° C. for 30 min, 100 μL of the prepared mixture containing 6 M guanidine hydrochloride, 50 mm Tris and 10 mm DTNB was added to terminate the reaction. After 15 minutes of incubation, the absorbance was measured at 412 nm. Finally, TrxR/Trx-1 activity %=(A$_{test}$-A$_{kb}$)/(A$_{control}$-A$_{kb}$), that is, the relative percentage of TrxR/Trx-1 activity was the activity inhibited by adding 2'-deoxyguanosine derivatives relative to the activity without 2'-deoxyguanosine derivatives. The data were fitted into a concentration response curve with a variable slope, and the IC$_{50}$ value was calculated from the curve. The experimental results are shown in Table 1.

TABLE 1

Inhibition of TrxR/Trx-1 activity by 6-dithio-substituted-2'-deoxyguanosine derivatives

| Compound | A | B | C | D | 6-thio-dG | PX-12 | Cladribine |
|---|---|---|---|---|---|---|---|
| $IC_{50}$ (μM) | 31.71 | 9.78 | 47.73 | 4.26 | >100 | 2.55 | >100 |

It can be seen from table 1 that PX-12, a Trx-1 inhibitor in clinical stage II, was used as a positive control, and commercially available Cladribine, a sulfur-containing anticancer drug with a structure similar to 2'-deoxyguanosine, and 6-thio-2'-deoxyguanosine (6-thio-dG), a candidate anticancer drug, were used as the negative control, some of these new compounds showed good TrxR/Trx-1 inhibitory activity, and the TrxR/Trx-1$IC_{50}$ of compound B and compound D reached 9.78 m and 4.26 M respectively, which was close to the positive control PX-12, which provided a new basis for the research of preparing cancer therapeutic drugs targeting Trx.

Biological Experiment 2:

MTT Assay—Inhibitory Effect of 6-dithio-substituted-2'-deoxyguanosine Derivatives on Tumor Cell Growth We measured the tumor cell growth inhibitory activity of candidate compounds by MTT assay. Human tumor cells in logarithmic growth phase were digested with 0.25% pancreatin for a certain time, centrifuged, re-suspended and counted with a blood cell counting plate to prepare a cell suspension, and the cell suspension was adjusted to 1.0× $10^4$-1×$10^5$ cells/mL. The cell suspension was inoculated into a 96-well culture plate, 100 μL per well, and cultured in an incubator with saturated humidity, 37° C. and 5% $CO_2$ for 24 hours until the cells completely adhered to the wall. The test compound was diluted to the required concentration with a complete medium, the complete medium of the 96-well culture plate inoculated with human tumor cells was sucked out, a medicament-containing medium was added, 100 μL per well, the final concentration of DMSO was less than 0.1%, and the culture plate was put in an incubator for 48 hours. 10 μl of MTT was added to each well of the 96-well plate, and the culture was continued for 4 h. The culture was stopped and the culture solution in the well was carefully sucked off. 150 μL DMSO was added to each well, and shaken at a low speed for 10 min on a shaking table, so that the crystal was fully dissolved. The absorbance of each well was measured at OD 570 nm of an enzyme-linked immunosorbent assay instrument. At the same time, zeroing wells (the culture medium, MTT, dimethyl sulfoxide) and control wells (cells, a drug dissolution medium with the same concentration, a culture solution, MTT, dimethyl sulfoxide) were set up, and the cell growth inhibitory activity was calculated with the corresponding solvents as the control. 3-6 multiple wells in each group were set up with repetition of several times. Cell viability of control=$(A_{drug\ group} - A_{zeroing\ well})/(A_{control\ well} - A_{zeroing\ well})*100\%$. Drawing was drawn, the data were fitted into a concentration response curve with a variable slope, and $IC_{50}$ value was calculated from the curve. The experimental results are shown in Table 2.

TABLE 2

Tumor cell growth inhibition of 6-dithio-substituted-2'-deoxyguanosine derivatives ($IC_{50}$, μM)

| Cell strain | A | B | C | D | 6-thio-dG | PX-12 | Cladribine |
|---|---|---|---|---|---|---|---|
| NCM460 | >1000 | >1000 | >1000 | >1000 | >1000 | >1000 | >1000 |
| HCT116 | 1.27 | 2.66 | 21.82 | 1.09 | 17.50 | 34.54 | 28.45 |
| SW620 | 0.21 | 1.71 | / | / | >100 | 1.68 | >100 |
| HT29 | 4.55 | 3.02 | 7.37 | 4.24 | 3.04 | 3.37 | 9.44 |
| A375 | 0.60 | 0.52 | 3.06 | 0.37 | 0.40 | 2.98 | / |
| BGC | 6.09 | / | / | 11.70 | >100 | / | / |
| K562 | 9.885 | 10.134 | 28.732 | 15.732 | 23.342 | 21.657 | 7.863 |
| HepG2 | 10~50 | <10 | 10~50 | <10 | <10 | 10~50 | / |
| A549 | 30.8 | 13.52 | 35.79 | 31.12 | 33.59 | 7.43 | / |
| MCF7 | / | 15.56 | / | 41.31 | >100 | >100 | >100 |
| Bcap37 | 18.24 | 21.04 | 35.12 | 22.77 | >100 | >100 | >100 |

It can be seen from Table 2 that when the anti-tumor compound 6-thio-2'-deoxyguanosine (6-thio-dG), the Trx inhibitor PX-12 and the commercially available anti-tumor drug Cladribine with a similar structure of 2'-deoxyguanosine are taken as positive controls, test compounds A, B, C and D and positive controls have obvious inhibitory effects on the proliferation of human colon cancer cells HCT116, SW620, HT29 and human melanoma cells A375, followed by human gastric cancer cells BGC, human leukemia cells K562 and human liver cancer cells HepG2, and have relatively small inhibitory effects on human non-small cell lung cancer A549, human breast cancer cells MCF7 and Bcap37 Among them, the tested compounds have obvious effects on human colorectal cancer cell HCT116, and are superior to the positive control. Compared with the test compounds A and C, the test compounds B and D have more obvious inhibitory effects on tumor cell proliferation, which provides a direction for the preparation of cancer drugs, especially melanoma and colorectal cancer drugs.

Biological Experiment 3:

Tumor-Bearing Test in Nude Mice—Inhibitory Effect of 6-Dithio-Substituted-2'-Deoxyguanosine Derivatives on the Growth of Subcutaneous Transplanted Tumor Tissue in Nude Mice 1) Tumor-Bearing Mouse Model of Human Colon Cancer Cell Line HCT116

We took human colon cancer cell line HCT116 as the research object, and established a subcutaneous transplanted tumor model of human colon cancer in 32 immunodeficient nude mice. The 24th generation HCT116 cells in logarithmic growth phase were digested with pancreatin to prepare a single-cell suspension, and $1\times10^7$ cells were inoculated subcutaneously in the right armpit of male nude mice about 5 weeks old. After inoculation, cyclophosphamide (100 mg/kg) was injected intraperitoneally for two consecutive days. Tumor growth was observed in 9-10 days. On the 20th day after colon cancer cell HCT116 was implanted subcutaneously, nude mice were divided into 7 groups by a random number table method, including a test drug group, a positive control group and a blank control group. Specifically, group A: the compound A was administrated; Group B: the compound B was administrated; Group C: the compound C was administrated; Group D: the compound D was administrated; Group E: the compound 6-thio-DG was administrated; Group F: the compound PX-12 was administrated; Group G: blank group, without administration of any compound. Except group C with 3 rats and group G with 4 rats, all other 5 groups had 5 rats, they mice were labeled and injected by tail vein once every two days for 24 days, 12 times, with the dose of compound A being 2 mg/kg for the first 8 times and 10 mg/kg for the last 4 times, and the dosages of other drugs being the same molar weights. The tumor volume was calculated by taking the length of the tumor as the longest diameter and the width as the corresponding vertical diameter, and the tumor volume V=(length×width$^2$) mm$^3$/2. 48 hours after the last treatment, blood was taken from the eyes, and then the animals were killed. Blood was centrifuged to get the supernatant, and then blood biochemical analysis was performed. Paraffin embedded sections of fixed tissues were stained with HE. The tumor mass in a frozen tissue was sectioned in a frozen state, and then stained by DAPI and TUNEL to judge the apoptosis of the tumor tissue in nude mice. The experimental results are as follows.

Figure 1:
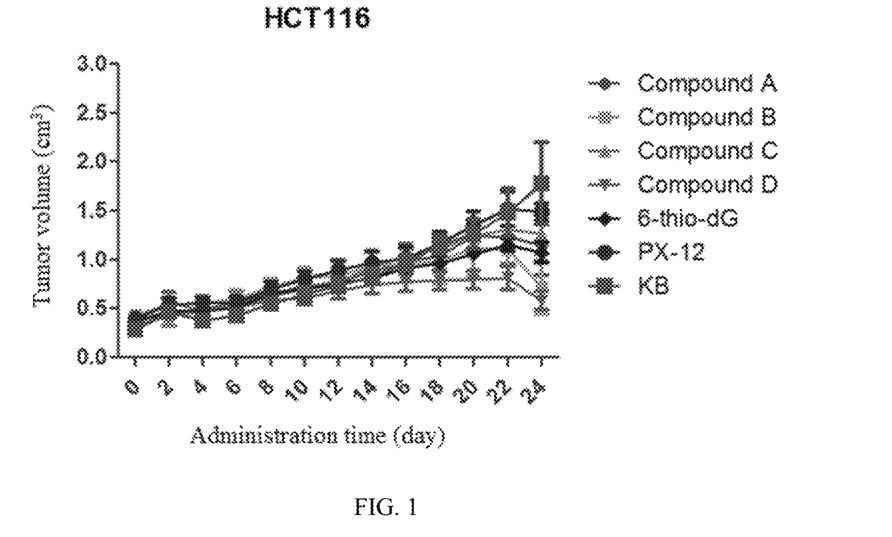
FIG. 1 is a graph showing the change of the tumor volume of nude mice in each group during the administration of a HCT116 cell tumor-bearing mouse model in the present invention.

The changes of tumor volume of nude mice in each group during administration are shown in FIG. 1. The variation slope of the tumor volume in nude mice of each group is D<B≈A≈6-thio-dG<PX-12<C<KB, so the inhibitory effect on the growth of subcutaneous transplanted tumor tissue in nude mice is: D>B≈A≈6-thio-dG>PX-12>C>KB. The ability of the test compound D to inhibit the growth of transplanted tumor tissue is stronger than that of positive control 6-thio-dG and PX-12, and the ability of test compounds B and A to inhibit the growth of transplanted tumor tissue is close to that of the positive control 6-thio-dG and stronger than that of the positive control PX-12. Compounds D, B and A showed the expected double-target synergistic effect.

Figure 2:
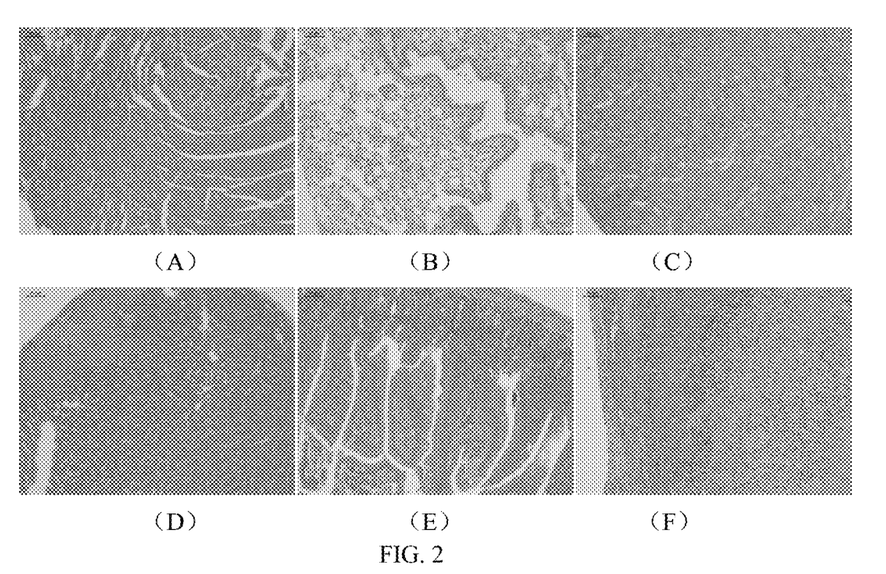
FIG. 2 is the result of HE staining after administration of the HCT116 cell tumor-bearing mouse model (group D), in which (a) is heart, (b) is lung, (c) is kidney, (d) is liver, (e) is intestine and (f) is a tumor tissue.

The results of HE staining are shown in FIG. 2. The toxic and side effects of the compounds can be judged by observing the morphology of each tissue. The results show that there is no obvious difference between the groups and the compounds have no obvious toxic and side effects.

Figure 3:
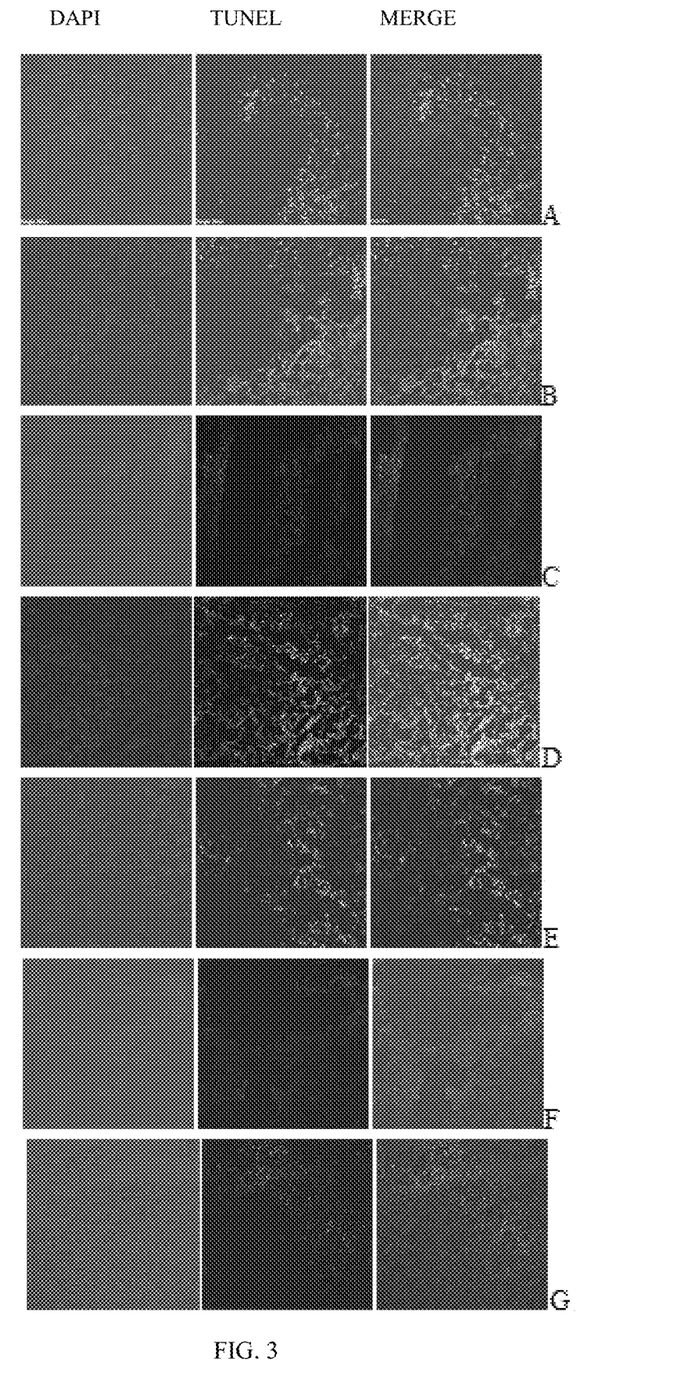
FIG. 3 is a graph of DAPI (living cells), TUNEL (apoptotic cells) and MERGE (superimposed) staining results of tumor tissues of each group after administration of the HCT116 cell tumor-bearing mouse model in the present invention, where A: administering a compound A; B: administering a compound B; C: administering a compound C; D: administering a compound D; E: administering a compound 6-thio-DG; F: administering a compound PX-12; G: blank group, administering a solvent.

The result of TUNEL staining is shown in FIG. 3, and the apoptosis rate can be calculated by the proportion of apoptosis dye staining in tumor tissues, so as to infer the extent of apoptosis in each group: D group>A group≈B group≈E group (6-thio-dG group)>C group>F group (PX-12 group) >G group (KB group). It is basically consistent with the inhibition of the tumor volume growth in nude mice.

Test results of blood biochemical indexes of nude mice in each group during administration are shown in Table 3.

TABLE 3

Test results of blood biochemical indexes of nude mice in each group during the administration of HCT 116 cell tumor-bearing mouse model

| Index | Group | | | | | | |
|---|---|---|---|---|---|---|---|
| | A | B | C | D | E | F | G |
| Total protein (g/L) | 52.6 | 50.7 | 51.6 | 54.2 | 51.8 | 56.9 | 60.2 |
| Albumin (g/L) | 24.8 | 26.3 | 27.9 | 25.0 | 29.8 | 33.0 | 39.7 |
| Alanine aminotransferase (U/L) | 33.3 | 105.9 | 25.5 | 28.2 | 44.3 | 30.8 | 32.9 |
| Aspartate aminotransferase (U/L) | 153.4 | 254.4 | 128.2 | 122.2 | 172.4 | 169.0 | 193.2 |
| Total bilirubin (μmol/L) | 0.40 | 0.90 | 0.80 | −1.00 | −0.10 | −0.90 | −1.10 |
| Alkaline phosphatase (U/L) | 36.0 | 31.0 | 33.7 | 31.5 | 49.6 | 44.2 | 56.0 |
| BUN (mmol/L) | 10.7 | 14.8 | 9.00 | 8.80 | 11.5 | 8.10 | 10.6 |
| Creatinine (μmol/L) | −0.80 | 8.67 | 6.67 | −3.0 | 12.0 | 3.20 | −11.5 |
| Glucose (mmol/L) | 2.21 | 2.29 | 2.99 | 3.51 | 3.12 | 1.47 | 2.14 |
| Potassium ion (mmol/L) | 7.56 | 6.26 | 6.17 | 6.43 | 7.18 | 7.64 | 7.76 |
| Sodium ion (mmol/L) | 155.6 | 158.0 | 159.0 | 157.5 | 158.8 | 155.8 | 161.0 |
| Chloride ion (mmol/L) | 113.8 | 124.0 | 120.5 | 115.3 | 120.8 | 109.9 | 104.8 |
| Triglyceride (mmol/L) | 0.84 | 0.52 | 1.15 | 0.70 | 1.10 | 1.18 | 2.67 |
| Total cholesterol (mmol/L) | 2.99 | 2.76 | 2.65 | 3.21 | 2.62 | 2.53 | 3.37 |
| Creatine kinase (U/L) | 1896 | 2169 | 980.7 | 1597 | 2125 | 1434 | 2183 |

It can be seen from Table 3 that there is substantially no significant difference in blood biochemical indexes among the groups of nude mice.

2) Human Melanoma Cell A375 Tumor-Bearing Mouse Model

We further studied the inhibitory effect of the compound D on human malignant melanoma by using A375 tumor-bearing mouse model. The method was basically the same as above. Dacarbazine (DTIC) is the first-line drug for melanoma. The designed administration groups were: compound D 10 mg/kg group; 6-thio-dG+PX12 combined drug group (the dose is equivalent to twice the molar amount of the compound D); DTIC 20.4 mg/kg group (the dose is equivalent to 4 times the molar amount of the compound D) and blank solvent group. The experimental results are shown in FIG. 4.

Figure 4:
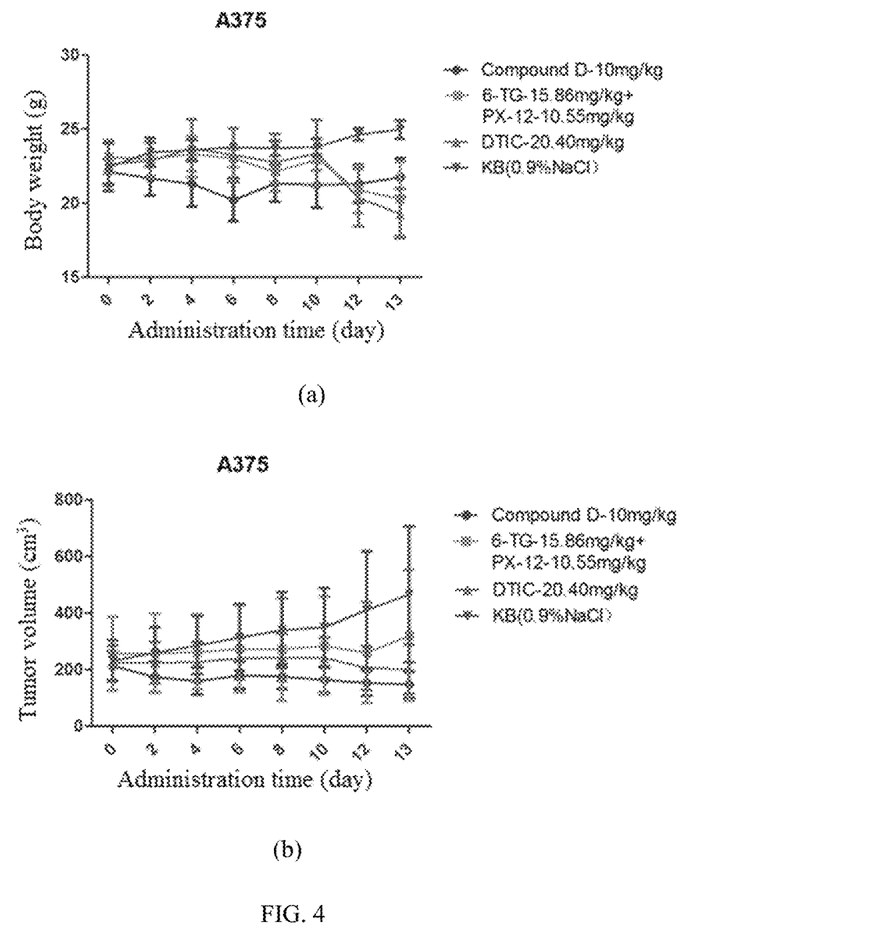
FIG. 4 is a graph showing changes of the body weight and tumor volume of nude mice in each group during administration of an A375 cell tumor-bearing mouse model, where

The results showed that when the dose of the compound D was one fourth of that of the positive control drug DITC, the antitumor effect of the compound D was significantly higher than that of DITC, and the antitumor effect was also significantly higher than that of 6-thio-dG and PX-12 com- bined drug group at twice the molar dose (see FIG. 4). The results showed that the inhibitory activity of the compound D on human malignant melanoma was significantly higher than that of DITC, and from the point of view of the rat body weight, although the body weight of the compound D group decreased rapidly at the initial stage of administration, it began to increase gradually after 6 days of administration, and after 13 days of administration, the body weight was significantly higher than that of DITC group, 6-thio-dG and PX-12 combination group, indicating that the body could quickly reverse the toxicity after continuous administration. In addition, compared with the combination of 6-thio-dG and PX-12, the compound D has significantly higher anti-tumor effect and lower toxicity than the combined drug group.

In addition, there was no significant difference in blood biochemical indexes among the groups, and no obvious toxicity was shown.

What is claimed is:

1. A method of treating colon cancer, comprising administering to a subject in need thereof a composition comprising a 6-dithio-substituted-2'-deoxyguanosine compound of formula I:

Formula I wherein R is C1-8 alkyl, C1-8 fluoroalkyl, C1-8 chloroalkyl, C1-8 hydroxyalkyl, C1-8 ketoalkyl, —(C1-4 alkyl) R1, —(C1-4 alkyl) NH$_2$, —(C1-4 alkyl) NH (C1-4 alkyl), phenyl selectively substituted by R2, a 5-membered aromatic ring selectively substituted with R2, C3-6 cycloalkyl selectively substituted with R2, or a 5 to 6-membered heteroaromatic ring containing at least one nitrogen and selectively substituted with R2;

R1 is phenyl, phenyl selectively substituted with —F, —Cl, —OH, —NH$_2$, —C1-4 alkyl, —OCH$_3$, —CONH$_2$ or —CONHCH$_3$, or a 5 to 6-membered heteroaromatic ring containing at least one nitrogen atom and selectively substituted with R2; and R2 is C1-4 alkyl, —CN, —OH, —OMe, —NH$_2$, —NHMe, —N(CH$_3$)$_2$, —F, —CF$_3$, —CO(C1-4 alkyl), —COCH$_2$CH$_2$OH, or —CONHCH$_3$.

2. The method according to claim 1, wherein the 6-dithio-substituted-2'-deoxyguanosine compound is a compound having a structure selected from the group consisting of:

A

B

C, and

D